United States Patent [19]

Arrighi et al.

[11] Patent Number: 5,259,951
[45] Date of Patent: Nov. 9, 1993

[54] PROCESS FOR THE PURIFICATION OF FACTOR VIII AND FACTOR VIII OBTAINED BY SAID PROCESS

[75] Inventors: Silvana Arrighi, Rieti; Maria G. Borri, Siena; Costante Ceccarini, Castelnuovo Berardenga, all of Italy

[73] Assignee: SCLAVO S.p.A., Siena, Italy

[21] Appl. No.: 713,071

[22] Filed: Jun. 11, 1991

[30] Foreign Application Priority Data

Jun. 12, 1990 [IT] Italy ................ 20610 A/90

[51] Int. Cl.$^5$ ................................. B01D 15/04
[52] U.S. Cl. ............................. 210/660; 210/656; 210/669; 210/749; 210/781; 210/782; 436/161; 436/176; 436/177; 530/383; 530/416; 530/417
[58] Field of Search ............... 210/656, 660, 663, 669, 210/666, 667, 198.2, 749, 781, 782; 436/161, 176, 177, 178; 530/383, 416, 417, 420, 421; 514/2

[56] References Cited

U.S. PATENT DOCUMENTS

| | | | |
|---|---|---|---|
| Re. 29,698 | 7/1978 | Fekete et al. | 530/383 |
| 4,361,509 | 11/1982 | Zimmerman et al. | 424/101 |
| 4,495,175 | 1/1985 | Chavin et al. | 530/383 |
| 4,543,210 | 9/1985 | Mitra et al. | 530/383 |
| 4,739,039 | 4/1988 | Vasquez et al. | 514/2 |
| 4,743,680 | 5/1988 | Mathews et al. | 210/656 |
| 4,883,598 | 11/1989 | Riethorst et al. | 210/656 |
| 4,952,675 | 8/1990 | Mathews et al. | 530/383 |

FOREIGN PATENT DOCUMENTS

| | | | |
|---|---|---|---|
| 383645 | 8/1990 | European Pat. Off. | 530/383 |
| 2650393 | 2/1991 | France | 530/383 |
| 8604486 | 8/1986 | PCT Int'l Appl. | |
| 9005140 | 5/1990 | World Int. Prop. O. | 530/383 |

OTHER PUBLICATIONS

L. R. Snyder and J. J. Kirkland, "Introduction to Modern Liquid Chromatography", John Wiley & Sons, Inc, NY, p. 190 (1979).
Herring et al., Journal of Chromatography, 326, pp. 217-224 (1985).
Brettler et al., Blood, vol. 73, No. 7, pp. 1859-1863 (1989).
Heimburger et al., Arzneim-Forsch/Drug Res., 31(1), Nr. 4, pp. 612-622 (1981).
Morfini et al., Thrombosis Research, 56, pp. 169-178 (1989).
Andersson et al., Medical Sciences, vol. 83, pp. 2979-2983 (1985).
Schwinn et al., Arzneim-Forsch./Drug Res., 39(II), Nr. 101, pp. 1302-1305 (1989).
Morgenthaler, Thromb Haemostas, 47 (2), pp. 124-127 (1982).
Austen, British Journal of Haematology, 43, pp. 669-674 (1979).

*Primary Examiner*—Robert A. Dawson
*Assistant Examiner*—Sun Uk Kim
*Attorney, Agent, or Firm*—Birch, Stewart, Kolasch & Birch

[57] ABSTRACT

A method for the purification of Factor VIII from human plasma is described, wherein a solution comprising Factor VIII is purified by using ion exchange chromatographic columns. Factor VIII obtained by said method is also described.

21 Claims, No Drawings

PROCESS FOR THE PURIFICATION OF FACTOR VIII AND FACTOR VIII OBTAINED BY SAID PROCESS

TECHNICAL FIELD OF THE INVENTION

The present invention relates to a process for the purification of Factor VIII from human plasma comprising treating a solution containing Factor VIII to an ion exchange chromatographic column, applying high ionic strength saline solutions at acid pH as equilibrating buffer and as eluent for the adsorbed Factor VIII and collecting the eluate in presence of stabilizers and optionally of an antiprotease.

STATE OF THE ART

The increasing importance attained by Factor VIII in the substitution therapy of haemophilia A has made it highly desirable to develop processes enabling said product to be obtained in higher amounts and higher purity. The current conventional processes for obtaining Factor VIII, which are essentially based on centrifugation, precipitation, chromatography and filtration techniques and which start from a cryoprecipitate [see N. Heimburger, H. Schwinn, P. Gratz, G. Luben, G. Kumpe and B. Herchenham: "Factor VIII concentrate, highly purified and heat-treated in solution" Arzneim.-Forsch./ Drug research 31 (1), 4, 619–622 (1981); S. W. Herring, K. T. Shitanishi, K. E. Moody and R. K. Enns: "Isolation of human factor VIII:C by preparative high-performance size-exclusion chromatography" J. of Chromatography 326: 217–(1985); H. Schwinn, A. Smith and D. Wolter: "Progress in purification of virus-inactivated Factor VIII concentrates" Arzneim.-Forsch./ Drug Research 39(II) 10 (1989)] allow a product to be obtained, that exhibits a specific activity, usually ranging from 2 to 100 U.I. Factor VIII:C per mg protein, and consequently not fully satisfactory. On the other hand, the cloning and/or purifying processes using immune-affinity chromatography [see D. B. Brettler, A. D. Forserberg, P. H. Levine, J. Fetillo, K. Lamon and J. Sullivan: "Factor VIII:C concentrate purified from plasma using monoclonal antibodies: human studies" Blood, 73, 1859–1863 (1989) L. O. Anderson, N. Forsman, K. Huang, K. Larsen, A. Lundin, B. Pavlu, H. Sandberg, K. Sewerin and J. Smart: "Isolation and characterisation of human Factor VIII concentrate: molecular forms in commercial Factor VIII concentrate, cryoprecipitate and plasma" Proc. Natl. Acad. Sci. USA, 83, 2979–2983 (1986) ; M. Morfini, D. Rafanelli, E. Filimberti, S. Cionotti, E. Piazza, G. Longo and P. Rossi Ferrini: "Protein content and factor VIII complex in untreated, treated and monoclonal factor VIII concentrates" Thrombosis Research, 56, 169–178 (1989)] truly allow a product of remarkable specific activity to be obtained, but however possess the serious drawback of a likelihood of contamination by virus, heterologous proteins and DNA residues from the host cell. Thus the product obtained by such processes needs to be thoroughly purified and tested to verify the absence of likely contaminants before its administration. The need of a developed process allowing the production of a product of higher specific activity but free of the aforementioned drawbacks is therefore evident.

DETAILED DESCRIPTION OF THE INVENTION

The process according to the present invention enables the preparation of Factor VIII of very high purity (specific activity higher than 300 U.I./mg protein) and free of the above mentioned drawbacks, by making use of an ion exchange chromatography process and applying high ionic strength saline solutions at acid pH, which permit the removal of undesired proteins without, however, destabilizing the biological activity. Following such a treatment, the osmolarity and concentration conditions of the solution are restored and the solution is stabilized and pasteurized according to known techniques. The process of chromatographic purification of the invention is carried out by using chromatographic columns containing an anion exchange resin such as Q-Sepharose fast flow (Pharmacia) and an equilibration buffer (TC) consisting of 10–30 mM Tris, 150–300 mM NaCl, 5–15 mM $CaCl_2$ at pH 6.4–6.8. The chromatography is operated at flow rate of 20–30 cm/h (by a diameter/height of the column ratio of 1/¾) and loading 10–20 mg protein per ml resin. The solution comprising Factor VIII at specific activity of 1.6–2 U.I. is fed into the column; unbound proteins and the von Willebrand factor are removed by washing the resin with the aforementioned TC buffer and the Factor VIII:C adsorbed upon the resin is eluted with an elution buffer (TE) consisting of 10–30 mM Tris, 450–650 mM NaCl, 5–15 mM $CaCl_2$, pH 6.4–6.8. Factor VIII:C solution, eluted from the column, is collected and stabilized with:

| Albumin 5% | 0.2–1.25 mg/ml eluted solution, |
|---|---|
| heparin | 0.02–0.125 U.I./ml eluted solution, |
| PEG 4000 | 0.006 mg/ml eluted solution | and optionally also lysine or histidine 10 mM solution as antiprotease. The disclosed process allows at least 150 times increase in purity of the solution with a recovery higher than 80% calculated on the starting product. The stabilized eluate is concentrated, disfiltrated and further concentrated up to a final volume of ¼ of the initial volume. The solution is then stabilized with PEG 4.000 to the end concentration of 0.7 g/l and finally it may either be frozen as such or submitted to pasteurization, desalting, concentration, distribution into vials and lyophilization according to well known methods using those techniques.

Further advantages and features of the process of the present invention will be more properly understood in the light of the following non-limiting example.

EXAMPLE

1° STAGE

About 2000 l fresh frozen human plasma are thawed with continuous stirring, up to a temperature of 0°–5° C. in a 2500 l vessel equipped with water cooling jacket at 20°–30° C. The cryoprecipitate (CP) is collected by cold precipitation on a low speed centrifuge, Westfalia type (6000–8000 rpm), or high speed, type Sharples type (12000–17000 rpm) fed with a membrane pump at speed varying from 14 to 20 l per minute, depending on the diameter of the rotor. The obtained cryoprecipitate (yield 8–10 gr/l ) may either be immediately subjected to the next purification phase or frozen (at −80° C.) in aliquots of about 1 Kg each and arranged in 2 cm thick slabs.

2° STAGE

Each Kilogram cryoprecipitate is solubilized at 25°-30° C., for about one hour with gentle stirring, with 3-4 volumes distilled water comprising 3-60 U.I. heparin per ml final solution. A 2% water suspension of aluminium hydroxide maintained at the same temperature is added always with stirring to the solution (160 ml/Kg cryoprecipitate).

Polyethylenglycol 4000 (PEG) is then added at the concentration from 2.5-4% and the contact is maintained for about 20-30 minutes with gentle stirring. The pH of the solution is adjusted to 6.4-6.6 with 1N acetic acid and the solution is then cooled at 9°-11° C. By means of low speed centrifugation the proteins adsorbed upon aluminium hydroxide and the cold insoluble proteins precipitated with PEG are removed. The precipitate represents a waste product (which can be used as starting material for the purification of other proteins, such as fibrinogen and fibrin glue), whereas the supernatant, i.e. Factor VIII solution, is further purified in the next stage.

3° STAGE

The solution described in the previous stage, obtained as seen by conventional techniques and having specific activity of 1-2 U.I./mg protein, is loaded onto a chromatography column, containing an anion exchange resin, having the following features:
a) diameter/height column ratio 1/$\frac{3}{4}$;
b) applied resin: Q-Sepharose fast flow (Pharmacia);
c) equilibration buffer (TC): 20 mM Tris, 250 mM NaCl, 10 mM $CaCl_2$, pH 6.6;
d) flow rate 24.5 cm/h (constant for the different chromatographic phase);
e) alimentation 18-20 U.I. factor VIII/ml resin corresponding to 10-20 mg protein / ml resin.

The unbound proteins are removed by washing the resin with 3-5 column volumes TC buffer. Factor VIII adsorbed upon the resin is eluted with 4 column volumes elution buffer TE 20 mM Tris, 550 mM NaCl, 10 mM $CaCl_2$, pH 6.6. The Factor VIII solution eluted from the column is collected in a vessel and the following stabilizers are added thereto:

| Albumin 5% | 0.2-1.25 mg/ml eluted. |
|---|---|
| heparin | 0.02-0.125 U.I./ml eluted, |
| PEG 4000 | 0.006 mg/ml eluted. |

The stabilized eluate is then concentrated to $\frac{1}{2}$ volume, disfiltrated versus two volumes 0.1M glycine, 0.13M NaCl, 0.005M $Na_3$ citrate buffer pH 7, and further concentrated to $\frac{1}{2}$ volume (final volume=$\frac{1}{4}$ of the starting volume) paying attention to equilibrate the membranes of the ultrafiltration system with the elution buffer TE. For the ultrafiltration system hollow fibre cartridges with cutoff 30 Kd and surface not lower than 0.1-0.2 m² per Kg of starting cryoprecipitate are used. The solution, stabilized with PEG 4000, to the final concentration of 0.7 gr/l may either be frozen at −80° C. or further processed as described according to the stages hereinafter, which are conventional operative techniques.

4° STAGE

The solution of pure Factor VIII is stabilized with:

| glycine | 60 gr/kg solution. |
|---|---|
| lysine | 145.9 gr/kg solution, |
| $CaCl_2.2H_2O$ | 0.294 gr/kg solution. |
| saccharose | 1.2 kg/kg solution. |

During the addition (as listed) of the stabilizers, the pH of the solution is adjusted and maintained at 7.45-7.55 with NaOH 1N. Should frozen Factor VIII solutions be used in this stage, they firstly need to be thawed and brought at 25° C., then stirred at such a temperature for about one hour before being stabilized. The stabilized solution is maintained with stirring at 35° C. for about one hour in order to achieve the complete solubilization of saccharose (perfectly clear solution), thereafter it is pasteurized at 60° C.±1° C. for 10 hours. After pasteurization the solution is slowly cooled (at least 15 minutes to 50° C.), then it is filtered on clarifying filter and diluted 1:1 (v/v) with 0.13M NaCl, 0.1M glycine buffer, pH 7.1 ql (TF).

5° STAGE

The diluted solution is concentrated to the starting volume (before stabilization) by means of a hollow fibre ultrafiltration system, with cutoff 30 Kd and a surface not lower than 0.1-0.2 m² per Kg of starting cryoprecipitate. The stabilizers are removed and then, the physiological conditions of the solution are re-established by diafiltration versus 2.5 volume buffer TF. The final solution is concentrated up to the desired values of U.I./ml, filtrated on clarifying filters and sterilized on 0.2μ pore sterilizing filters. The sterile solution is thereafter aseptically dispensed into vials and frozen at −40° C. The vials are then lyophilized by low pressure slow temperature increase from −40° C. to +30° C. The features of Factor VIII obtained by the present process are reported in Table I.

TABLE I

| U.I. factor VIII: C/ml | 100-120 U.I./ml |
|---|---|
| Total proteins | 4.9-5.3 mg/ml |
| Added albumin as stabilizer | 4.8-5.0 mg/ml |
| Residue proteins from process | 0.1-0.3 mg/ml |
| Specific activity before stabilisation, U.I. VIII:C/protein | 300-1200 |
| Specific activity after albumin stabilisation | 18-24 |
| U.I. antigen von Willebrand (vW:RAg) | <25 U.I./ml |
| vW:RAg/VIII:C Ratio | <0.4 |
| Fibrinogen content | <0.06 mg/ml |
| Fibronectin content | <0.001 mg/ml |
| IgG content | <0.004 mg/ml |
| IgA content | <0.005 mg/ml |
| IgM content | <0.002 mg/ml |

We claim:
1. Process for the purification of Factor VIII from human plasma comprising passing a solution containing Factor VIII through an ion exchange chromatographic column using both as an equilibrating buffer and as an eluent for adsorbed Factor VIII, a high ionic strength saline solution at an acid pH of from 6.4 to 6.8 and eluting said adsorbed Factor VIII with said high ionic strength saline solution and collecting a recovered eluate in presence of stabilizers and optionally of an antiprotease.

2. Process according to claim 1, wherein said chromatographic column contains an anion exchange resin.

3. Process according to claim 2, wherein the anion exchange resin comprises quaternary amino groups.

4. Process according to claim 1, wherein the equilibrating buffer consists of 10-30 mM Tris, 150-300 mM NaCl, 5-15 mM CaCl$_2$ and pH is from 6.4 to 6.8.

5. Process according to claim 4, wherein the equilibrating buffer consists of 20 mM Tris, 250 mM NaCl, 10 mM CaCl$_2$ and pH is 6.6.

6. Process according to claim 1 wherein the eluent for Factor VIII consists of 10-30 mM Tris, 450-650 mM NaCl, 5-15 mM CaCl$_2$ and pH is from 6.4 and 6.8.

7. Process according to claim 6, wherein the eluent for Factor VIII is 20 mM Tris, 550 mM NaCl, 10 mM CaCl$_2$ and pH is 6.6.

8. Process according to claim 1 wherein the eluted Factor VIII is stabilized with:

| Albumin 5% | 0.2-1.25 mg/ml eluate, |
| --- | --- |
| heparin | 0.02-0.125 U.I. g/ml eluate, |
| PEG 4000 | 0.006 mg/ml eluate | and optionally an antiprotease.

9. Process according to claim 8, wherein lysine or histidine are used as antiprotease.

10. Process according to claim 9, wherein the antiprotease is used in concentration 10 mM.

11. Process for purification of Factor VIII from human plasma comprising:
A) thawing human fresh frozen plasma with stirring, permitting a cryoprecipitate to form and collecting the cryoprecipitate by centrifugation;
B) solubilizing the cryoprecipitate in distilled heparinized water to form a solution and, treating the solution with an aluminum hydroxide suspension and then with PEG 4000, adjusting the pH with acetic acid 1N to a value 6.4-6.6 and cooling the solution thereafter to 9°-11° C.; removing by centrifugation the proteins adsorbed upon aluminum hydroxide and those precipitated leaving a supernatant;
C) passing said supernatant obtained in the previous stage through a chromatographic column containing an anion exchange resin by using an equilibrating buffer which consists of 10-30 mM Tris, 150-300 mM NaCl, 1-15 mM CaCl$_2$ and pH 6.4 to 6.8; then washing the resin with the aforementioned buffer in order to eliminate the undesired proteins and then recovering the factor von Willebrand and Factor VIII:C by eluting with an eluent buffer consisting of 10-30 mM Tris, 450-650 mM NaCl, 5-15 mM CaCl$_2$ and pH 6.4 to 6.8; stabilizing the so recovered Factor VIII:C with:

| Albumin 5% | 0.2-1.25 mg/ml eluate, |
| --- | --- |
| heparin | 0.02-0.125 U.I. g/ml eluate, |
| PEG 4000 | 0.006 mg/ml eluate | concentrating, diafiltrating and further concentrating the obtained eluate solution up to a final volume equal to 174 starting volume;
D) pasteurizing, concentrating and dispensing the Factor VIII:C into vials and lyophilizing the Factor VIII:C.

12. Process according to claim 11, wherein the equilibrating buffer consists of 20 mM Tris, 250 mM NaCl, 10 mM CaCl$_2$ and pH is 6.6

13. Process according to claim 11, wherein the eluent buffer for Factor VIII is 20 mM Tris, 550 mM NaCl, 10 mM CaCl$_2$ and pH is 6.6.

14. Process for the purification of Factor VIII from human plasma comprising passing a solution containing Factor VIII through an ion exchange chromatographic column using as equilibrating buffer a high ionic strength saline solution consisting of 10-30 mM Tris, 150-300 mM NaCl, 5-15 mM CaCl$_2$ at pH from 6.4 to 6.8 and eluting an adsorbed Factor VIII with a high ionic strength saline solution consisting of 10-30 mM Tris, 450-650 mM NaCl, 5-15 mM CaCl$_2$ at the above said pH and collecting a recovered eluate in presence of stabilizers and optionally of an antiprotease.

15. Process according to claim 14, wherein the equilibrating buffer consists of 20 mM Tris, 250 mM NaCl, 10 mM CaCl$_2$ and pH is 6.6.

16. Process according to claim 14, wherein the eluent for Factor VIII is 20 mM Tris, 550 mM NaCl, 10 mM CaCl$_2$ and pH is 6.6.

17. Process according to claim 16, wherein said chromatographic column contains an anion exchange resin.

18. Process according to claim 17, wherein the anion exchange resin comprises quaternary amino groups.

19. Process according to claim 14, wherein the eluent Factor VIII is stabilized with:

| Albumin 5% | 0.2-1.25 mg/ml eluate. |
| --- | --- |
| heparin | 0.02-0.125 U.I. g/ml eluate. |
| PEG 4000 | 0.006 mg/ml eluate | and optionally an antiprotease.

20. Process according to claim 19, wherein lysine or histidine are used as antiprotease.

21. Process according to claim 20, wherein the antiprotease is used in concentration 10 mM.

* * * * *

UNITED STATES PATENT AND TRADEMARK OFFICE
CERTIFICATE OF CORRECTION

PATENT NO.  : 5,259,951
DATED       : November 9, 1993
INVENTOR(S) : Arrighi et al It is certified that error appears in the above-indentified patent and that said Letters Patent is hereby corrected as shown below:

Column 2

Line 43, change "disfiltrated" to --diafiltrated--.

Column 3

Line 56, change "disfiltrated" to --diafiltrated--.

Column 5

Claim 11

Line 52, delete "then recovering",

Line 53, before "Factor VIII:C" insert --then recovering--.

Signed and Sealed this

Ninth Day of April, 1996

Attest:

BRUCE LEHMAN

Attesting Officer

Commissioner of Patents and Trademarks